United States Patent [19]
Overell

[11] Patent Number: 5,256,553
[45] Date of Patent: Oct. 26, 1993

[54] MULTIPLE PROMOTER TRANSFORMING RETROVIRAL VECTORS

[75] Inventor: Robert W. Overell, Seattle, Wash.

[73] Assignee: Immunex Corporation, Seattle, Wash.

[21] Appl. No.: 772,637

[22] Filed: Oct. 8, 1991

Related U.S. Application Data

[63] Continuation of Ser. No. 554,160, Jul. 16, 1990, abandoned, which is a continuation of Ser. No. 107,126, Oct. 9, 1987, abandoned.

[51] Int. Cl.$^5$ .................. C12N 15/86; C12N 5/10; C12N 7/01; C12N 15/48
[52] U.S. Cl. .................. 435/172.2; 435/240.2; 435/320.1; 536/23.1; 935/27; 935/32; 935/57; 935/70
[58] Field of Search ............... 435/235.1, 320.1, 240.2; 424/93 A, 172.3; 536/23.1

[56] References Cited

U.S. PATENT DOCUMENTS 4,957,865 9/1990 Samarut et al. .................. 435/235.1

FOREIGN PATENT DOCUMENTS 0178996 4/1986 European Pat. Off. .
0235113 9/1987 European Pat. Off. .
0307248 3/1989 European Pat. Off. .
8903872 5/1989 PCT Int'l Appl. .

OTHER PUBLICATIONS

J.-K. Yee et al (1987) Proc. Natl. Acad. Sci. USA 84:5197–5201.
Hawley et al. "Handicapped retroviral vectors efficiently transduced foreign genes into hematopoietic stem cells," Proc. Natl. Acad. Sci. U.S.A. 84:2406–2410, 1987.
Yu et al., "Self-inactivating retroviral vectors designed for transfer of whole genes into mammalian cells", Proc. Natl. Acad. Sci. USA 83:3194 (May 1986).
Miller et al., "Infectious and Selectable Retrovirus Containing an Inducible Rat Growth Hormone Minigene", Science 225:993 (Sep. 1984).
Overell et al., "Stably Transmitted Triple-Promoter Retroviral Vectors and Their Use in Transformation of Primary Mammalian Cells", Molec. and Cell. Biol. 8(4):1803 (Apr. 1988).
Newbold et al., "Fibroblast immortality is a prerequisite for transformation by EJ c-Ha-ras oncogene" Nature 304 (5927):648 (Aug. 1983).
Emerman et al., "Quantitative Analysis of Gene Suppression in Integrated Retrovirus Vectors", Mol. and Cell. Biol. 6:792 (1986).
Rubenstein et al., "Construction of a retrovirus capable of transducing and expressing genes in multipotential embryonic cells", Proc. Natl. Acad. Sci. USA 81:7137 (Nov. 1984).
Overell, et al., "Nature and Specificity of Lymphokine Independence Induced by a Selectable Retroviral Vector Expressing v-src", Mol. and Cell. Biol. 7:3394 (Oct. 1987).
Armentano et al., "Effect of Internal Viral Sequences on the Utility of Retroviral Vectors", J. Virol. 61(5):1647 (May 1987).
Emerman & Temin, "High-Frequency Deletion in Recovered Retrovirus Vectors Containing Exogenous DNA with Promoters," J. Virol. 50:42 (1984).
Coffin, in Weiss, et al., eds., *RNA Tumor Viruses* vol. 2 (Cold Spring Harbor Laboratory, 1985) pp. 36–71.
Land et al., "Tumorigenic Conversion of Primary Embryo Fibroblasts Requires at Least Two Cooperating Oncogenes," Nature 304:596 (1983).
Land et al., "Behavior of myc and ras Oncogenes in Transformation of Rat Embryo Fibroblasts," Mol. Cell. Biol. 6:1917 (1986).

(List continued on next page.)

Primary Examiner—Richard A. Schwartz
Assistant Examiner—Johnny F. Railey, II
Attorney, Agent, or Firm—Morrison & Foerster

[57] ABSTRACT

A new class of oncogenic retroviral vectors is disclosed which comprise at least two oncogenes and a heterologous DNA sequence, each of which is independently transcribed in an infected or transfected cell under the control of a separate transcriptional control sequence.

17 Claims, 2 Drawing Sheets

OTHER PUBLICATIONS

Mann et al., "Construction of a Retrovirus Packaging Mutant and Its Use to Produce Helper-Free Defective Retrovirus," *Cell* 33:153 (1983).

Miller et al, "Generation of Helper-Free Amphotropic Retroviruses That Transduce a Dominant-Acting, Methotrexate-Resistant Dihydrofolate Reductase Gene," *Mol. Cell. Biol.* 5:431 (1985).

Miller et al., "Redesign of Retrovirus Packaging Cell Lines to Avoid Recombination Leading to Helper Virus Production," *Mol. Cell. Biol.* 6:2895 (1986).

Rapp et al., "Structure and Biological Activity of v-raf, a Unique Oncogene Transduced by a Retrovirus," *Proc. Natl. Acad. Sci. USA* 80:4218 (1983).

Schwartz et al., "Synergism of v-myc and v-Ha-ras in the In Vitro Neoplastic Progression of Murine Lymphoid Cells," *Mol. Cell. Biol.* 6:3221 (1986).

Wagner et al., "Transfer of Genes into Embryonal Carcinoma Cells by Retrovirus Infection: Efficient Expression from an Internal Promoter," *EMBO J.* 4:663 (1985).

MULTIPLE PROMOTER TRANSFORMING RETROVIRAL VECTORS

This application is a continuation of 07/554,160, filed Jul. 16, 1990, now abandoned, which is a continuation of application Ser. No. 07/107,126 filed Oct. 9, 1987, now abandoned.

BACKGROUND OF THE INVENTION

The present invention relates generally to DNA vectors useful for introducing new genetic material into mammalian and avian cells, and particularly to a new class of retroviral vectors capable of stably transforming primary mammalian cells to provide new genotypes which express heterologous DNA sequences.

Retroviral vectors provide an efficient means of gene transfer, particularly for cells which are difficult to transfect by other methods, or which are represented at a low frequency in mixed primary populations. In the replicative cycle of retroviruses, the RNA-based genomic complement of an infecting retrovirus is reverse-transcribed to provide DNA copies known as proviruses, which are stably incorporated into cellular DNA. Generally, infection by retrovirus does not kill infected cells, and a broad variety of cell types and host species are susceptible to infection in vivo and in vitro by certain amphotropic retroviruses. Coffin, in Weiss et al., eds., *RNA Tumor Viruses Vol.* 2 (Cold Spring Harbor Laboratory, 1985) pp 36-71, provides a review of progress in the use of retroviruses as vectors of foreign genes.

A number of genes have been expressed in retroviral constructs, principally by utilizing the transcriptional enhancer and promoter elements in the retroviral long terminal repeat (LTR). These flanking sequences provide the transcriptional signals required for expression of proviral DNA. For example, Miller et al., *Mol Cell. Biol.* 5:431 (1985), employed retroviral vectors containing a mutant dihydrofolate reductase (DHFR) gene under the transcriptional control of the Moloney murine leukemia virus (MoMLV) LTRs to confer increased methotrexate resistance to infected cells.

Retroviral vectors have been constructed in which inserted genes are expressed from single heterologous internal promoters. Such promoters include those from the SV40 early region, and the Herpes Simplex Virus thymidine kinase (HSVtk), mouse metallothionein and rat growth hormone genes. Internal promoters have been used to express selectable antibiotic resistance marker in infected mammalian cells. For example, Wagner et al., *EMBO J.* 4:663 (1985) constructed MoMLV-based vectors in which the selectable neomycin resistance gene neo was expressed under the control of an internal thymidine kinase (TK) promoter.

Preliminary experiments involving retroviral vectors incorporating more than one internal transcriptional promoter suggested that such constructions were ineffective expression vectors due to rearrangements of proviral DNA in infected cells. These rearrangements resulted in a partial deletion of one inserted cistron. In these experiments, Emerman and Temin, *J. Virol.* 50:42 (1984) assembled spleen necrosis virus (SNV)-based retroviral vectors containing the herpes simplex virus thymidine kinase (TK) and mouse α-globin genes, each including its own promoter Infected cells selected for expression of the HSVtk cistron consistently contained proviruses with deletions of the α-globin promoter. However, viruses having the α-globin gene inserted without its promoter were stable during several cell passages under the same conditions. It was proposed that the deletions occurred because the active α-globin promoter prevented efficient transcription of the HSVtk cistron in this vector, perhaps by epigenetic suppression of gene expression, or via transcriptional overlap interference. These results suggested that retroviral vectors containing multiple internal promoters could not be used effectively to co-express inserted sequences in singly infected cells.

Acutely oncogenic retroviruses contain a DNA sequence, known generically as an oncogene (onc), which is capable of transforming infected cells to a cancerous or malignant phenotype. Known retroviral oncogenes are not required for normal viral replication but appear to have evolved by transduction of normal cellular genes, known as cellular proto-oncogenes, into the viral genome. Under the control of a strong retroviral promoter, or by mutation or rearrangement, cellular proto-oncogenes acquire transforming capacity. Approximately sixty oncogenes are known, which form several principal genera on the basis of sequence homology and presumed function. In general, expression of a single oncogene is insufficient for the full transformation of primary mammalian cells. Coinjection strategies employing separate retroviruses, each bearing a single oncogene, have previously been employed to achieve transformation of Primary mammalian cells. See, e.g., Schwartz et al., *Mol. Cell. Biol.* 6:3221 (1986), Land et al., *Nature* 304:596 (1983); Land et al., *Mol. Cell. Biol.* 6:1917 (1986). However, this approach is not practical with mixed primary populations if the observed infection frequency of the target cell is low. Construction and use of single retroviral vectors comprising two oncogenes under the control of independent transcriptional promoters has not been reported.

The present invention resulted from attempts to create a model system in which oncogene combinations capable of immortalizing primary lymphoid or hematopietic cells could be identified. In this work, retroviral vectors were constructed which expressed two oncogenes under independent transcriptional control. A drug-resistance marker under the control of a third promoter also was incorporated into the vectors to enable selection of infected cells expressing proviral DNA. The resulting vectors transformed taret cells to a drug resistant phenotype with high efficiency, while co-expressing the oncogene products. Retroviral vectors capable of independently expressing three or more distinct cistrons represent valuable gene transfer vehicles for transfection of primary mammalian cells.

SUMMARY OF THE INVENTION

The present invention provides a recombinant DNA provirus comprising (a) retroviral long terminal repeat sequences, LTR, comprising a transcriptional control sequence tcs1 and additional elements enabling integration of the provirus into cellular DNA of the host cell; (b) a second transcriptional control sequence tcs2; (c) a third trancriptional control sequence tcs3; (d) a first viral or cellular oncogene onc1; (e) a second viral or cellular oncogene onc2; (f) and a heterologous DNA sequence het; wherein onc1 and onc2 are different and onc1, onc2, and het are operably linked to tcs1, tcs2 and tcs3 such that expression of each DNA sequence in a host cell harboring the provirus is activated by an independent transcriptional control sequence without deletion or rearrangement of proviral DNA.

In vector embodiments, the invention provides plasmid vectors comprising a recombinant provirus as defined above and bacterial DNA sequences enabling replication of the vector in a host bacterium. The invention further provides infective virus particles comprising retroviral RNA transcribed from a provirus as defined above, produced in a host cell capable of viral packaging, and transformed cells comprising at least one copy of the provirus integrated into chromosomal DNA following transfection with a vector comprising a provirus of the invention or infection with an RNA-containing retrovirus of the invention, or cells derived from such transformed cells. In process embodiments, the invention provides various methods of transforming mammalian cells using the recombinant virus or vectors comprising the recombinant provirus.

BRIEF DESCRIPTION OF THE FIGURES

In FIGS. 1 and 2 open boxes represent structual genes and shaded boxes represent promoters. Arrows represent transcription initiation sites for each of the three promoters. Straight lines represent retroviral sequences and wavy lines represent flanking plasmid sequences.

DETAILED DESCRIPTION OF THE INVENTION

Figure 1:
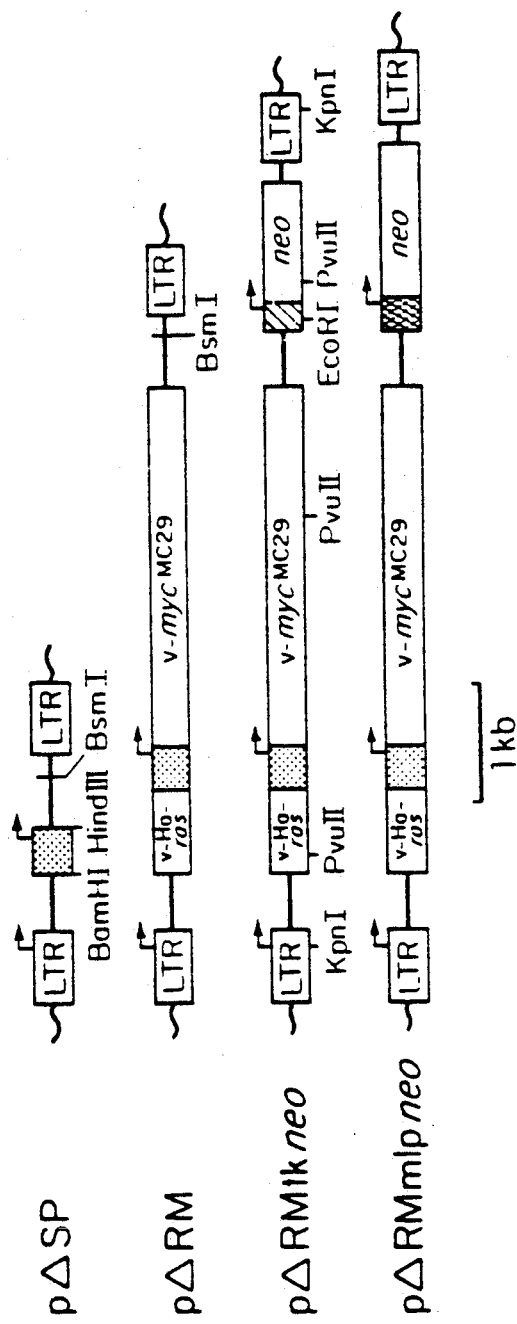
FIG. 1 schematically illustrates the retroviral vectors pΔSP, pΔRM, pΔRMtkneo and pΔRMm1pneo.

The retroviral vectors of this invention are designed to permit expression of three inserted genes (two oncogenes and at least one heterologous gene, e.g., a selectable marker) from independently transcribed mRNAs. In one embodiment, one gene is transcribed under control of the vector LTR and two from heterologous internal transcriptional promoters. The proviral components of the vectors of this invention can be efficiently transcribed and packaged in appropriate host or host-/helper virus systems to provide infective virus. They express multiple cistrons in infected cells without rearrangement or deletion, unlike previously disclosed retroviral constructs comprising more than one heterologous internal promoter. These vectors are considered capable of transforming primary mammalian cells to an immortalized neoplastic state.

As used herein, "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. "Recombinant," as used herein, means that a particular DNA sequence is the product of various combinations of cloning, restriction, and ligation steps resulting in a construct having a sequence distinguishable from homologous sequences found in natural systems. Generally, recombinant DNA sequences according to this invention are assembled from cloned fragments and short oligonucleotide linkers, or from a series of oligonucleotides.

"Retrovirus" refers to a member of the class of viruses which replicate using a virus-encoded, RNA-directed DNA polymerase, or reverse transcriptase, to replicate a viral RNA genome to provide a double stranded DNA Intermediate which is incorporated into chromosomal DNA of an avian or mammalian host cell. Retroviruses adaptable for use in connection with the present invention can be derived from any avian or mammalian cell source, and are preferably amphotropic, meaning that they are capable of infecting host cells of several species. A characteristic feature of retroviral genomes is the retroviral long terminal repeat, or LTR, which is an untranslated region found in slightly variant forms at the 5' and 3' ends of the retroviral RNA genome. When incorporated into DNA as a provirus, the retroviral LTR includes a short direct repeat sequence at each end, a tRNA primer binding site, and signals for initiation of transcription by RNA polymerase II and 3' cleavage and polyadenylation of RNA transcripts. The promoter or transcriptional signals provided by retroviral LTR sequences are generally efficient.

"Provirus" refers to DNA reverse transcript of a retrovirus which is stably integrated into chromosomal DNA in a suitably host cell, or a cloned copy thereof present in a vector or other construction. Forward transcription of the provirus and assembly into infectious virus occurs in the presence of an appropriate helper virus or in a cell line containing appropriate sequences enabling encapsidation without coincident production of a contaminating helper virus Mann et al., Cell 33:153 (1983) describe the development of cell lines (e.g., ψ2) which can be used to produce helper-free stocks of recombinant retrovirus. These cell lines contain integrated retroviral genomes which lack sequences required in cis for encapsidation but which provide all necessary gene products in trans to produce intact virions. The integrated mutant provirus cannot itself be packaged but can these cells can encapsidate RNA transcribed from a recombinant retrovirus introduced into the same cell. The resulting virus particles are infective, but replication-defective, rendering them useful vectors which are unable to produce infective virus following introduction into a cell lacking the complementary genetic information enabling encapsidation. Encapsidation in a cell line harboring trans-acting elements encoding an ecotropic viral envelope e.g. ψ2 provides ecotropic (limited host range) progeny virus. Alternatively, assembly in a cell line containing amphotropic packaging genes [PA 317; ATCC CRL 9078; Miller et al., Mol. Cell. Biol. 6:2895 (1986)] provides amphotropic (broad host range) progeny virus.

"Transfection" means introduction of the retroviral vectors of the present invention into a recipient cell by DNA-mediated gene transfer such that the proviral DNA is integrated into cellular DNA. "Infection" means the process by which infecting retrovirus particles are absorbed by cells, resulting in reverse transcription of the retroviral RNA genome and integration of the resulting provirus into cellular DNA. "Transformation" refers to process in which a cell's genotype is changed as a result of cellular uptake of exogeneous DNA or RNA.

Retroviruses to be adapted for use in accordance with this invention can be derived from many avian or mammalian hosts. However, a requirement for use is that the virus be capable of infecting cells which are to be the recipients of the new genetic material to be transducer using the retroviral vectors. Examples of retroviruses include avian retroviruses such as avian erythroblastosis virus (AMV), avian leukosis virus (ALV), avian myeloblastosis virus (ABV), avian sarcoma virus (ASV), Fujinami sarcoma virus (FuSV), spleen necrosis virus (SNV), and Rous sarcoma virus (RSV); bovine leukemia virus (BLV); feline retroviruses such as feline leukemia virus (FeLV) or feline sarcoma virus (FeSV); murine retroviruses such as murine leukemia virus (MuLV), mouse mammary tumor virus (MMTV), and murine sarcoma virus (MSV); rat sarcoma virus (RaSV); and primate retroviruses such as human T-cell lymphotropic viruses 1 and 2 (HTLV-1, 2), and simian sarcoma virus (SSV). Many other suitable retroviruses are known to those skilled in the art. A taxonomy of retroviruses is provided by Teich, in Weiss et al, eds., *RNA Tumor Viruses*, 2d ed., Vol. 2 (Cold Spring Harbor Laboratory, New York, 1985) pp 1-16. Particularly preferred retroviruses for use in connection with the present invention are the murine retroviruses known as Moloney murine sarcoma virus (MoMSV), Harvey murine sarcoma virus (HaMSV) and Kirsten murine sarcoma virus (KiSV). The MoMSV genome can be obtained in conjunction with a pBR322 plasmid sequence pMV (ATCC 37190), while a cell line producer of KiSV in K-BALB cells has been deposited as ATCC 163.3. A deposit of a plasmid (pRSVneo) derived from pBR322 including the RSV genome and an intact neo drug resistance marker is available as ATCC 37198. A plasmid (pPBI01) comprising the SNV genome is available as ATCC 45012. It would be a matter of routine molecular biology to obtain the viral genome from these sources and construct a useful replication defective retroviral vector. The resulting recombinant retrovirus would thus be capable of integration into the chromosomal DNA of an infected host cell, but once integrated, be incapable of replication to provide infective virus, unless the cell in which it is introduced contains another proviral insert encoding functionally active trans-acting viral proteins.

"Transcriptional control sequence" is a generic term used throughout the specification to refer to nontranscribed DNA sequences, such as initiation signals, enhancers, and promoters, which induce or control transcription of downstream structural sequences with which they are operably linked. "Downstream" refers to the direction of transcription. "Internal" refers to a vector or proviral location between retroviral LTRs. The vectors and other constructs of the invention require multiple independent transcriptional control sequences. Such enhancers or promoters can be derived from viral or mammalian genomes, and are preferably constitutive in nature. Exemplary and useful promoters include the SV40 early or late promoters, the HSVtk promoter, the Adenovirus 2 major later promoter, or other viral promoters derived from polyoma virus, bovine papilloma virus, or other retroviruses or adenoviruses. The entire Adenovirus 2 genome has been sequenced (see below) and is present in pAV1, deposited as ATCC 37125. Similarly, there are numerous sources of SV40 DNA including commercial vendors such as New England Biolabs. Using well-known restriction and ligation techniques, appropriate transcriptional control sequences can be excised from various DNA sources and integrated in operative relationship with intact structural genes to be expressed using the retroviral constructs of this invention.

"Vector" refers to DNA vehicle, for example, a plasmid, comprising bacterial sequences enabling replication of the vector DNA in a suitable bacterial host cell. Vectors within the scope of the present invention also include copies of at least one molecularly cloned provirus, which includes the transcriptional elements noted above in independent operative association with at least three separate structural DNA sequences which are transcribed into mRNA and translated into protein when proviral sequences are expressed in transformed host cell. At least two of the structural DNA sequences incorporated into the provirus are oncogenes as described below.

The proviral DNA sequences and vectors of the present invention are designed to be particularly useful in transformation of primary mammalian cells. Primary cell cultures consist of cells freshly removed from an organism and maintained in an appropriate nutrient medium. The cultures are typically heterogeneous mixtures of many cell types, each of which can be induced to replicate a limited number of generations. Primary cells are thus distinguishable from cell lines, which have been immortalized as a result of an ancestral transformation event or other mutation resulting in continuous or indefinite growth in culture.

In order to provide transforming capability, the RNA or DNA constructs of the present invention incorporate at least two oncogenes, which can be derived from viral or cellular genomes or mammalian or avian chromosomal DNA. In general, infection of an appropriate target cell with an acutely oncogenic retrovirus leads to oncogenic transformation. Although the mechanism of oncogenesis not clearly understood, numerous viral oncogenes, or v-oncs, as well as their cellular homologues, known as proto-oncogenes or c-oncs, have been catalogued. There are several postulated mechanisms by which c-oncs acquire transforming capability, including control by strong viral promoters, gene copy amplification, addition of viral enhancer sequences, rearrangement, and mutation. For purposes of the present invention, suitable oncogenes include any oncogenic sequences or sequences substantially homologous to oncogenic sequences which are capable of transforming a primary mammalian host cell when co-expressed with another transforming oncogene. Partial lists of oncogenes are provided by Bishop et al., in Weiss et al., eds., *RNA Tumor Viruses*, Volume 1 (Cold Spring Harbor Laboratory, N.Y. 1984) pp 1004-1005, and Watson et al., *Molecular Biology of the Gene*, 4th Ed., Vol. II, (Benjamin Cummings, Menlo Park, Ca.) pp 1037. Included are the known oncogenes such as src, yes, abl, fps, fes, erbB, fms, ros, kit, mos, raf, H-ras, K-ras, sis, myc, myb, fos, ski, and erbA. Many oncogene products have tyrosine-specific protein kinase or serine/threonine protein kinase activity, or appear to be homologues of growth factors, growth factor receptors, or are nuclear proteins with unknown function. Many oncogenes can be obtained from public collections of deposited biological materials. Thus, v-raf is present in the plasmid pF4 deposited as ATCC 45010 [Rapp et al., *Proc. Natl. Acad. Sci. USA* 80:4218 (1983): v-myc$^{mc29}$ is available as ATCC 45014; and v-Ha-ras is a genetic component of ATCC 41047.

The heterologous DNA sequence het which is a component of the DNA and RNA constructs of the present invention can be any gene for which expression in a primary host cell is desired, including a third oncogene. The het gene product may provide a dominant selectable marker for infected cells, for example, an antibiotic resistance phenotype such as neo (G418 resistance), hygro (hygromycin resistance), or gpt (mycophenolic acid resistance). Alternatively the het gene product may complement a metabolic deficiency in a specialized host strain, i.e., thymidine kinase activity in tk⁻ cells, or hypoxanthine phosphoribosyl transferase (HPRT) activity in HPRT⁻ cells. Such selectable markers, as well as appropriate host cell lines for complementary markers, are widely available among researchers. Of potentially greater commercial significance are constructs in which het encodes a gene product having value or utility independent of the environment in which it is translated, for example, specific immunoglobulins, serum proteins, viral or tumor cell antigens, or biologically active molecules such as enzymes, hormones, growth factors, or receptors for hormones or growth factors, or homologues of the foregoing.

Useful plasmid vectors for amplifying the retroviral genetic elements in bacterial hosts prior to transfection are constructed by inserting a retroviral DNA sequence encoding the elements described previously in a vector including one or more phenotypic selectable markers and an origin of replication to ensure amplification within a bacterial host. A preferred prokaryotic host for vector amplification is *E. coli*, although others may also be employed as a matter of choice. Thus, a useful mammalian/bacterial shuttle vector can comprise a selectable marker and bacterial origin of replication derived from commercially available plasmids comprising genetic elements of the well known cloning vector pBR322 (ATCC 37017). Appropriate methods for growth of plasmid-bearing hosts and isolation of plasmid DNA are described by Maniatis, *Molecular Cloning: A Laboratory Manual* (Cold Spring Harbor Laboratory, 1982.)

The following examples describe construction of retroviral vectors which permitted co-expression of three inserted genes from independent transcriptional promoters in singly infected cells. Several triple promoter vectors were constructed with various combinations of oncogenes and selectable drug resistance genes. All were found to express three mRNAs of the expected size in infected cells without rearrangement or deletion. One vector, which expressed the v-Ha-ras and v-myc oncogenes and neo marker, was characterized in detail. This retrovirus did not undergo rearrangement during the process of infection, as judged by Southern analysis, and infection of primary rat embryo fibroblasts demonstrated that the ras/myc cotransformed cells could be selected in G418. In the examples, all procedures involving use of DNA-modifying enzymes, for example, restriction endonucleases and DNA polymerases, were conducted according to the instructions provided by the manufacturer. Other standard nucleic acid manipulation technologies are substantially similar to those disclosed by Maniatis, supra. All probes were labelled with $^{32}$P.

The cells and culture conditions employed were as follows. BALB/3T3 cells (clone A31, ATCC CCL 163) and ψ2 cells [Mann et al., *Cell* 33:153 (1983)] were grown in Dulbecco's Modified Eagle's Medium (DMEM; Gibco) supplemented with 10% calf serum, 2 mM glutamine, 50 U/ml penicillin, and 50 U/ml streptomycin. All cells were grown at 37° C. in a humidified atmosphere of 10% $CO_2$ in air.

EXAMPLE 1

Two triple promoter retroviral vectors were constructed by inserting the neo G418 antibiotic resistance gene, under the control of the hsvtk or adenovirus 2 major late promoter, at a BsmI site of the dual promoter retroviral vector pΔRM, which contains the v-Ha-ras and v-myc oncogenes. The resulting triple-promoter vectors were designated pΔRMtkneo and pΔRMmlpneo respectively, and are depicted in FIG. 1.

pΔRM was constructed from an intermediate vector pΔSP, which was in turn derived from pLSDL [Miller et al., *Mol. Cell. Biol.* 5:431 (1985)] substantially as described below. First, the dhfr sequences between the HindIII and NcoI sites of pLSDL were removed and a BglII linker inserted at this position such that the HindIII site was preserved; second, using site-directed mutagenesis (AGGT→AGGC), the MoMSV-derived splice donor was deleted at nucleotide 862 of pLSDL. pΔRM was constructed from pΔSP by inserting a SacI-PstI fragment of the v-Ha-ras gene from pHB11 [Ellis et al., *Nature* 292:506 (1981)] at the BamHI site of pΔSP using BamHI-linkers, and then inserting a BstEII-SphI fragment of the v-myc gene encoding p110$^{gag-myc}$ [Vennstrom et al., *J. Virol.* 39:625 (1981)] at the BglII site using a BglII linker. To construct pΔRMtkneo, pΔRM was digested with BsmI, blunt-ended with T4 DNA polymerase, and a fragment containing the neo gene under the control of the hsvtk promoter was inserted at this position. This tk-neo cassette consisted of a PvuII-BglII fragment spanning the hsvtk promoter [McKnight et al., *Science* 217:316 (1982)]ligated to a BglII-SmaI fragment of the neo gene [Beck et al., *Gene* 19:327 (1982)]. pΔRMmlpneo was constructed from pΔRM using a similar strategy but with a blunt-ended fragment containing the neo gene under the control of the adenovirus 2 major late promoter (mlp). The mlp-neo cassette consisted of a XhoI-PvuII fragment of the Adenovirus 2 major late promoter (nucleotides 5,778–6,072 of the sequence disclosed by Gingeras et al., *J. Biol. Chem.* 257:13475 (1982), ligated to a HindIII-SmaI fragment of the neo gene.

FIG. 1 illustrates the structure of retroviral vectors pΔSP, pΔRM, pΔRMtkneo and pΔRMmlpneo. In FIG. 1, stippled boxes represent the SV40 early region promoter, the hatched box the HSVtk promoter and the cross-hatched box the adenovirus 2 major late promoter. Arrows represent transcription initiation sites for each of the three promoters. Straight lines represent retroviral sequences derived from Moloney MSV/MuLV [Miller et al., *Mol. Cell. Biol.* 5:431 (1985)]; wavy lines represent flanking plasmid sequences. LTR indicates the MoMSV long terminal repeat sequences.

The resulting constructs were transfected into ψ2 cells [Mann et al., *Cell* 33:153 (1983)] and virus-producing clones were isolated following selection in G418. As shown in Table 1, below, the ΔRMtkneo and ΔRMmlpneo retroviruses conferred both focus formation and G418 resistance on BALB/3T3 cells with similar titers, while the parental ΔRM retrovirus conferred only focus formation.

The biological activity of each of the three cistrons in the ΔRMtkneo retrovirus was tested by infecting primary rat embryo fibroblasts (REFs) and selecting for G418 resistance. It has previously been shown that cotransfection of activated ras and myc oncogenes induces morphological transformation and focus formation in primary REFs, whereas transfection of either oncogene alone are ineffective [Land et al., *Nature* 304:596 (1983); Land et al., *Mol. Cell. Biol.* 6:1917 (1986)]. As controls, parallel cultures of REFs were infected with the ΔH virus, or with viruses expressing a selectable marker and either v-myc or v-Ha-ras alone. $2.5 \times 10^4$ REFs were infected with $\sim 5 \times 10^3$ CFU of each virus in 1 ml for 20 hours in the presence of 4 pg/ml polybrene. After a further 24 hours the cells were selected for G418 resistance or focus formation. After a further ten days of growth the cells were fixed with methanol, stained with methylene blue, and examined under magnification.

Only the ΔΔRMtkneo virus induced the formation of drug-resistant REF colonies with a grossly transformed morphology typical of that induced by ΔRM in focus assays and that seen following cotransfection of REFs with activated ras and v-myc oncogenes. This overt morphological transformation was not observed in drug-resistant colonies of REFs which arose following infection with retroviral vectors encoding a selectable marker and either v-Ha-ras or v-myc alone.

Total cell RNA from clones of ΔRMtkneo-infected, G418 resistant BALB/3T3 cells, ΔRMtkneo-infected BALB/3T3 cells selected in bulk for G418 resistance, a clone of ψ2 cells producing the ΔRMtkneo virus, ΔRMmlpneo-infected BALB/3T3 cells selected in bulk for G418 resistance, and a clone of ψ2 cells producing the ΔRMmlpneo virus was subjected to northern analysis. The predicted transcript sizes to the nearest 50 bp, not including poly(A) tails, for ΔRMtkneo are 7050 nucleotides transcribed from the vector 5' LTR, 5450 nucleotides transcribed from the SV40 promoter; and 1700 nucleotides transcribed from the hsvtk promoter (see FIG. 1). For ΔRHmpneo the predicted transcript sizes are 7300 nucleotides, 5750 nucleotides, and 2000 nucleotides. The latter transcript is transcribed from the adenovirus 2 major late promoter in ΔRMmlpneo.

In these experiments, 5 μg total cell RNA from the transfected ψ2 and infected BALB/3T3 cells was electrophoresed on a 1% agarose-formaldehyde gel as disclosed by Maniatis, supra, and analyzed by Northern hybridization with $^{32}$P-labeled antisense RNA transcripts of the neo and v-myc genes generated from an SP6 transcription system (Promega Biotech). While the neo probe hybridized to all three transcripts, a probe specific for the v-myc gene hybridized to the larger two transcripts only, as expected from the structure of these vectors. The relative positions of these mRNAs on the blot were consistent with their predicted sizes. Thus, blotting of total cell RNA using probe DNAs specific for the structural sequences of each cistron showed that the three expected vector-specific transcripts were expressed from the ΔRMtkneo and ΔRMmlpneo vectors. The sizes of the transcripts in the ψ2 and 3T3 lanes were indistinguishable, indicating that these three promoter vectors had been transmitted by retroviral infection without undergoing gross rearrangement. To assay for vector rearrangements at the clonal level, BALB/3T3 cells were infected with the ΔRMtkneo virus (MOI=$10^{-4}$) and cloned in G418. Northern analysis showed that all of the six clones isolated expressed vector-specific transcripts of the same size as those previously observed in bulk populations of ΔRMtkneo-infected 3T3 cells.

Genomic DNA was isolated from six independently isolated clones, and the integrated provirus analyzed by Southern hybridization (see Maniatis, supra) as follows.

EcoRI digests of genomic DNA were electrophoresed on 0.6% agarose gels which were then blotted onto nitrocellulose. Hybridizations were conducted for 20 hours at 42° in a buffer containing 50% formamide, using a nick-translated probe generated from a BglII-SmaI fragment of the neo gene. Blots were washed in 1×SSC at 68° and exposed at −70° C. with intensifying screens.

The results indicated that each clone contained a single proviral insertion, since the neo probe hybridized to a single EcoRI restriction fragment in each of the DNA samples. The different migration rates of these restriction fragments confirmed that the clones were independently infected isolates, since their size was determined by the single EcoRI site in the ΔRHtkneo vector and by the proximity of the EcoRI site in the genomic sequences 3' to the integrated provirus.

Two Southern hybridization strategies were used to assay for deletions or rearrangements of the ΔRMtkneo provirus in the infected 3T3 clones. To release the intact provirus, genomic DNA samples were digested with KpnI (which cuts once in each LTR), electrophoresed as described above, and Southern blots hybridized with a neo-specific probe. To assay for small deletions in the vicinity of the internal transcriptional promoters, the DNAs were digested with PvuII and blots hybridized with v-myc-specific probe. Nick-translated probes were generated from a BglII-SmaI fragment of the neo gene and a BstEII-SphI fragment of the v-myc gene.

In both cases the restriction fragments hybridizing with the probes were of the predicted sizes, were the same for each of the clones, and comigrated with digests of pΔRMtkneo DNA electrophoresed on the same gels. Thus, the triple promoter ΔRMtkneo retrovirus was transmitted without detectable rearrangements or deletions in each of six distinct clones of infected 3T3 cells selected for G418 resistance.

This experiment demonstrated that triple-promoter retroviral vectors can be transmitted by retroviral infection and stably maintained when selection is applied for expression of one of the three inserted cistrons. No rearrangements of the integrated ΔRHtkneo proviruses were detectable by Southern analysis and each triple-promoter vector expressed the three expected transcripts in infected cells. Additionally, the ΔRMtkneo virus expressed three gene products in a functional manner, as judged by the production of fully transformed, G418 resistant colonies of primary REFs.

EXAMPLE 2

Two additional triple-promoter vectors, designated ΔHsrcmyc and ΔHrafmyc, were constructed with the same promoter organization as the ΔRMtkneo vector described above. However, these vectors expressed the hph (hygro) gene, which confers resistance to hygromycin B on mammalian cells. The hygro gene has been found to be a preferred dominant selectable marker for lymphoid cells. To increase the level of v-myc expression, this gene was expressed from the HSVtk promoter in the ΔHsrcmyc and ΔHrafmyc vectors.

Figure 2:
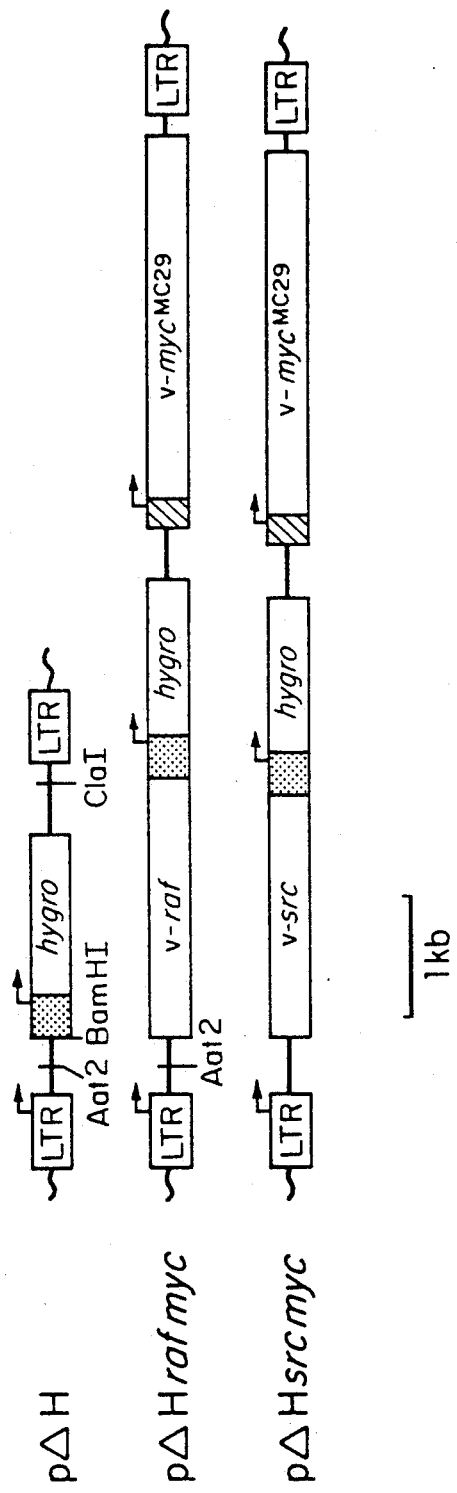
FIG. 2 depicts the retroviral vectors ΔHsrcmyc and ΔHrafmyc.

The structure of the retroviral vectors pΔH, pΔHrafmyc, and pΔHsrcmyc is schematically illustrated in FIG. 2, wherein vector segments are labeled as described in the legend to FIG. 1. To construct pΔH, pΔSP (Example 1) was digested with HindIII and the hph gene from pLG90 [Gritz, *Gene* 25:179 (1983) was inserted at this position with HindIII linkers. The hph gene confers resistance to hygromycin B on mammalian cells and is labeled hygro in FIG. 2. ΔHrafmyc was constructed from ΔH by removing the AatII-BamHI fragment from ΔH and replacing it with an AatII-BamHI fragment containing the v-raf oncogene from the plasmid pF4 [Rapp et al., *Proc. Natl. Acad. Sci. USA* 80:4218 (1983) ATCC 45010], then inserting a fragment containing the v-myc gene under the control of the HSVtk promoter into the blunted ClaI site of ΔH. The tk-myc cassette consisted of the PvuII-BglII fragment of the HSVtk promoter ligated to a BglII v-myc fragment from pΔRM. ΔHsrcmyc was constructed from ΔH by inserting a BamHI-linkered NcoI-EcoRI fragment encoding v-src from pSRA-2 [DeLorbe et al., *J. Virol.* 36:50 (1980)] at the BamHI site of ΔH. The tk-myc cassette was inserted as in ΔHrafmyc.

To verify expression of ΔHrafmyc and ΔHsrcmyc in infected and transfected cells, total cell RNA from the (1) ψ2 clone producing the ΔHrafmyc retrovirus, (2) BALB/3T3 cells infected with ΔHrafmyc and selected in bulk for hygromycin resistance, (3) a ψ2 clone producing the ΔHsrcmyc retrovirus and (4) BALB/3T3 cells infected with ΔHsrcmyc and selected in bulk for hygromycin resistance were subjected to Northern analysis as described in Example 1, above. The predicted RNA transcript sizes of both ΔHrafmyc and ΔHsrcmyc are similar for both constructs and include components of ~8500, 5700, and 3700 nucleotides, not including poly(A) tails. The blot was hybridized with a v-myc probe consisting of a $^{32}$P-labeled antisense RNA transcript of the v-myc gene generated by SP6 RNA polymerase transcription. Each sample included three hybridizing transcripts having migration rates on the gel which were consistent with their predicted sizes.

EXAMPLE 3

This experiment illustrates transfection of ψ2 cells using the retroviral vectors of this invention to and generation of infective but replication-defective virus, which was then assayed for the capacity to transduce focus-formation and drug resistance to the BALB/3T3 murine cell line.

The ΔRMtkneo and ΔRMmlpneo retroviral vectors constructed as described in Example 1, and the ΔHrafmyc and ΔHsrcmyc vectors of Example 2, were transfected into ψ2 cells [Mann et al., *Cell* 33:153 (1983)] and virus-producing clones were isolated following selection in G418 or hygromycin B.

Each virus was harvested from the supernatant of a clone of transfected ψ2 cells. ψ2 cells were transfected using a calcium phosphate procedure disclosed by Corsaro et al., *Somat. Cell Genet.* 7:603 (1981). Cells were replated into selective medium containing either G418 (500 μg/ml) or hygromycin B (300 μg/ml) 24 hours after transfection. After 7-10 days growth, well-separated colonies were trypsinized using glass cloning cylinders. A clone producing virus was grown to confluence, then fed with drug-free medium. After an overnight incubation an aliquot of supernatant was taken for assay.

In this assay, exponentially dividing BALB/3T3 cells were removed from culture dishes with trypsin-EDTA (Gibco) and seeded at a density of $2.5 \times 10^4$ cells per 35 mm tissue culture well (Costar). After 24 hours incubation, the medium was aspirated and replaced with serial dilutions of virus-containing supernatant (1 ml/well) in medium containing 4 pg/ml polybrene (Sigma). All supernatants were centrifuged at 2000 rpm for 10 minutes prior to use to remove viable cells. Cells were incubated with virus overnight, then the supernatant was aspirated and replaced with fresh growth medium. Cells were selected for antibiotic resistance after a further 24 hours' growth by adding antibiotic at the concentrations described above. Cells were then incubated for seven days, then refed with drug containing media and, after a total of 12-14 days growth, fixed with 100% MeOH and stained with methylene blue. For selection for focus formation, infected cells were fed every three to four days post-infection with drug-free media and fixed and stained after a total of 12-14 days' growth.

The results set forth in Table 1, below, show that the triple-promoter retroviruses conferred both focus formation and G418 or hygromycin B resistance on BALB/3T3 cells with similar titers, while the parental ΔRM retrovirus conferred only focus formation. In Table 1, CFU refers to colony-forming units, and FFU to focus-forming units.

TABLE 1

| Titers of Retroviruses Produced by ψ2 Cells | | | |
|---|---|---|---|
| Virus | Neo$^r$ CFU/ml | Hygro$^r$ CFU/ml | FFU/ml |
| ΔRM | 0 | ND | $1.3 \times 10^5$ |
| ΔRMtkneo | $4.6 \times 10^4$ | ND | $4.0 \times 10^4$ |
| ΔRMmlpneo | $3.2 \times 10^4$ | ND | $3.4 \times 10^4$ |
| ΔHrafmyc | ND | $1.7 \times 10^5$ | $3.1 \times 10^5$ |
| ΔHsrcmyc | ND | $3.3 \times 10^4$ | $2.3 \times 10^4$ |

The present invention is not limited to the specific embodiments disclosed herein, but rather encompasses other modifications and aspects which those skilled in the art, having the benefit of the present specification, may produce or practice. The scope of present invention is intended to be limited only by the following claims.

What is claimed is:

1. A recombinant DNA provirus comprising:
   (a) retroviral long terminal repeat sequences, LTR, including a 5' LTR comprising a transcriptional control sequence tcs1 and additional elements enabling integration of the provirus into cellular DNA of the host cell, and a 3' LTR;
   (b) a second transcriptional control sequence tcs2;
   (c) a third transcriptional control sequence tcs3;
   (d) a first viral or cellular oncogene onc1;
   (e) a second viral or cellular oncogene onc2; and
   (f) a heterologous DNA sequence het;
   wherein onc1 and onc2 are different and onc1, onc2, and het are operably linked to tcs1, tcs2, and tcs3 such that expression of each of the DNA sequences onc1, onc2 and het in a host cell stably transformed as a result of infection with a retrovirus harboring RNA transcribed from said DNA provirus is activated by an independent transcriptional control sequence without deletion or rearrangement of proviral DNA; and
   wherein tsc2 and tcs3 are internal transcriptional control sequences located between the 5'LTR and the 3'LTR.

2. A recombinant DNA provirus according to claim 1, wherein onc1 and onc2 are capable of stably transforming a primary mammalian cell.

3. A recombinant DNA provirus according to claim 2, wherein onc1 and onc2 are viral oncogenes.

4. A recombinant DNA provirus according to claim 3, wherein het is an oncogene.

5. A recombinant DNA provirus according to claim 3, wherein het encodes a dominant selectable marker.

6. A recombinant DNA provirus according to claim 3, wherein het encodes an immunoglobulin.

7. A recombinant DNA provirus according to claim 3, wherein onc1 and onc2 are selected from the group consisting of v-ras, v-raf, v-myc, and src.

8. A recombinant DNA provirus according to claim 3, having the formula 5′LTR-onc1-tcs2-onc2-tcs3-het-3′LTR.

9. A plasmid vector comprising bacterial DNA sequences enabling replication of the vector in a host bacterium and a recombinant provirus according to claim 1.

10. A plasmid vector comprising bacterial DNA sequences enabling replication of the vector in a host bacterium and a recombinant provirus according to claim 8.

11. Infectious virus comprising retroviral RNA transcribed from a provirus according to claim 1 in a host cell capable of viral packaging.

12. Infectious virus comprising retroviral RNA transcribed from a provirus according to claim 8 in a host cell capable of viral packaging.

13. Infectious virus according to claim 11, which is assembled in a host cell capable of amphotropic viral packaging.

14. A mammalian cell, or cell derived therefrom, comprising at least one copy of a provirus according to claim 1 integrated into chromosomal ONA as result of transfection with a vector comprising said provirus, or infection with an RNA-containing retrovirus transcribed from said provirus.

15. A method for transforming a mammalian cell, comprising transfecting proviral DNA into the cell using a vector according to claim 9.

16. A method for transforming a mammalian cell, comprising contacting the cell with an infectious virus according to claim 11 under conditions promoting infection of the cell by the retrovirus.

17. A method for transforming a primary mammalian cell, comprising contacting the cell with an infectious virus according to claim 11 under conditions promoting infection of the cell by the retrovirus.

* * * * *